(12) United States Patent
Horsmon et al.

(10) Patent No.: US 12,324,773 B1
(45) Date of Patent: Jun. 10, 2025

(54) HORIZONTAL WHOLE-BODY EXPOSURE APPARATUS

(71) Applicant: U.S. Army Combat Capabilities Development Command, Chemical Biological Center, Apg, MD (US)

(72) Inventors: Michael S Horsmon, Joppa, MD (US); Dennis B Miller, Rising Sun, MD (US)

(73) Assignee: United States Army as Represented by the Secretary of the Army, Washington, DC (US)

( * ) Notice: Subject to any disclaimer, the term of this patent is extended or adjusted under 35 U.S.C. 154(b) by 909 days.

(21) Appl. No.: 17/502,733

(22) Filed: Oct. 15, 2021

(51) Int. Cl.
 *A61G 10/00* (2006.01)
 *A61M 16/12* (2006.01)

(52) U.S. Cl.
 CPC ........... *A61G 10/005* (2013.01); *A61M 16/12* (2013.01); *A61M 2250/00* (2013.01)

(58) Field of Classification Search
 CPC ................................................ A61M 2250/00
 See application file for complete search history.

(56) References Cited

PUBLICATIONS

Horsmon et al., âDevelopment of a Single Animal Dynamic Airflow Whole-Body Exposure Apparatus,â published Aug. 1, 2021. (Year: 2021).*
Fairchild et al., âCollection Efficiency of Field Sampling Cassettes,â LA-8640-MS (1980). (Year: 1980).*
Su et al., âEvaluation of physical sampling efficiency for cyclone-based personal bioaerosol samplers in moving air environments, J. Environ, Monitor., 14(9): 2430-7 (2012). (Year: 2012).*

* cited by examiner

*Primary Examiner* — Thaddeus B Cox
(74) *Attorney, Agent, or Firm* — Ulysses J. Biffoni; Timothy M. Barlow

(57) ABSTRACT

This disclosure relates to a horizontal whole body chamber (HWBC) for conducting whole-body exposure analyses therein. The HWBC is configured to provide a uniform distribution of a test material within an air flow to achieve reliable whole body exposure. The HWBC achieves uniform mixing over short distance lengths to provide whole body exposure chambers that are practical for smaller animals and lessen the consumption of laboratory space.

22 Claims, 3 Drawing Sheets

HORIZONTAL WHOLE-BODY EXPOSURE APPARATUS

GOVERNMENT INTEREST

Figure 1:
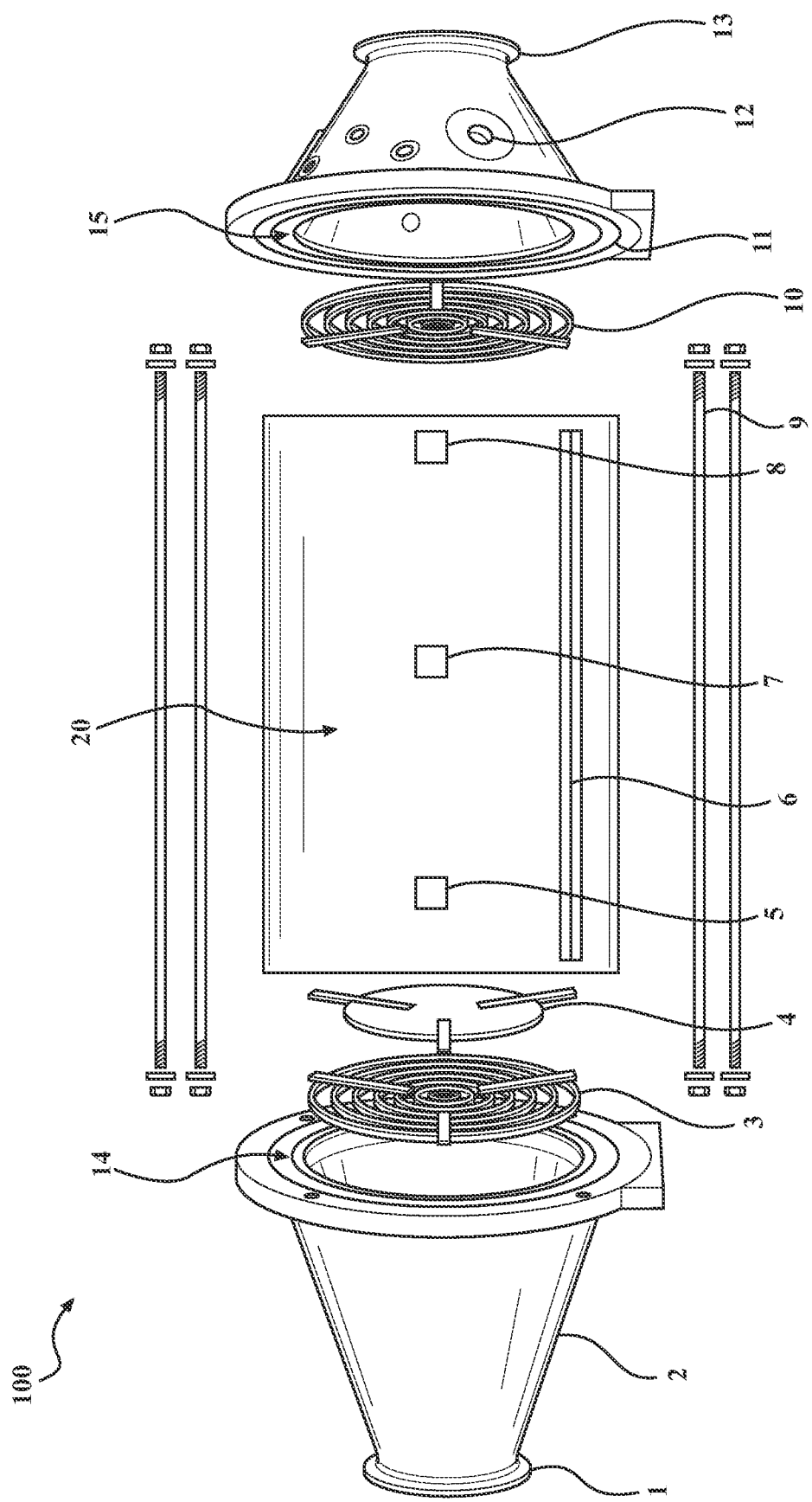

The invention described herein may be manufactured, used, and/or licensed by or for the United States Government.

FIELD OF THE INVENTION

This disclosure relates to a horizontally aligned exposure chamber that can accommodate the whole-body of a subject.

BACKGROUND

Inhalation toxicology studies take the form of several primary routes of exposure depending on the specific goals of the research question under investigation. These can generally be divided into intra-tracheal instillation, nose-only inhalation, head-only inhalation, and whole-body (WB) inhalation. One of the most difficult, yet most realistic, methods is the whole-body exposure. This is especially important when attempting to research the effects of compounds that have the ability to penetrate the skin. Only whole-body exposure can accurately represent the pharmacokinetic properties and capture the pharmacodynamic response for compounds that exhibit toxicity through inhalation and percutaneous exposure.

Current whole-body exposure apparatuses fall into being either large stainless steel and glass/lexan chambers with a volume of over 250 L or small vertical acrylic/lexan chambers with a volume under 10 L. Both systems are reviewed by Wong et al. (*Toxicologic pathology* 35.1 (2007): 3-14). The large chambers provide a suitable option for exposing large animals or larger groups of small animals, but are unnecessary and superfluous for studies involving groups of small animals or single exposures of small or medium sized animals. The acrylic/lexan cylinder chambers are a feasible option for individual exposures of small animals, but their small point source inlet in the middle of the chamber ceiling provides no mechanism for even distribution of a test material, especially in instances for short (2-5 minute) exposure durations that are often encountered with highly toxic materials. Further, the choice of acrylic or lexan for construction can react with some harsher reagents, particularly those that may be utilized for decontamination purposes, such as alcoholic sodium hydroxide. Accordingly, there is a need for a reusable, well-distributed chamber that can provide efficient exposure to animals of any size.

SUMMARY OF THE INVENTION

The present disclosure concerns an enclosed chamber that includes a horizontal chamber tube operably connected at a proximal end to a first end cap and at a distal end to a second end cap. The chamber is of a material with a cross sectional dimension that defines a hollow space along the length of the horizontal chamber tube. The first end cap includes an inlet and at least one Stairmand disk. The second end cap includes an outlet. In some aspects, the inlet and the outlet are operably connected through the hollow space to allow passage of a test gas through the enclosed chamber. In further aspects, the enclosed chamber is configured to disperse an aerosol uniformly within 1 to 3 cm of the proximal end of the chamber tube.

In some aspects, the first end cap may include at least two Stairmand disks. In further aspects, the first end cap may include at least three Stairmand disks. In some aspects, the first end cap may further include a screen. In further aspects, the first end cap may be connected to the horizontal cylindrical chamber tube through a mechanical seal. In certain aspects, the mechanical seal is an O-ring or a gasket.

In some aspects of the present disclosure, a vacuum source may be attached to the outlet. In other aspects, a forced air source may be attached to the inlet.

In other aspects of the present disclosure, the first end cap and the second end cap are retained against the horizontal cylindrical chamber tube by an applied force. In certain aspects, a threaded rod or a clamp is placed on the first end cap and/or second end cap for the applied force.

In some aspects, the inlet and outlet of the end caps are configured to provide said test gas flow of between 1 to 3 linear feet per minute through the enclosed chamber.

In some aspects of the present disclosure, there may be at least one sensor placed in the hollow space.

In certain aspects of the present disclosure, the hollow space of the enclosed chamber is in a horizontal cylinder shape. In other aspects, the horizontal chamber tube may be of glass, steel, or an organic polymer.

In some aspects of the present disclosure, the first end cap and the second end cap are of a truncated conical shape. In further aspects, one or more ports may be present on the first end cap and/or the second end cap to access the test gas as it passes through the enclosed chamber.

In some aspects, the enclosed chamber is configured to disperse a test gas uniformly within 1 to 3 cm of the proximal end of the chamber tube. In certain aspects, the test gas may be a particle aerosol or a gas atmosphere.

The present disclosure also concerns methods for assessing whole-body exposure to a test gas in a subject. The steps of the methods may include placing the subject in the hollow space of the enclosed chamber as described herein. The methods may also include providing a test gas at the inlet, providing a source to cause the test gas to flow through the hollow space of the enclosed chamber; and incubating the subject for a test period of time.

In some aspects, the source may be from a forced air source at the inlet or a vacuum source at the outlet. In certain aspects, the vacuum may be applied at a pressure to move the test gas through the enclosed chamber at a rate of 1 to 3 linear feet per minute.

In other aspects, the methods may include obtaining a sample of the test gas from the enclosed chamber during the test period of time. In certain aspects, a telemetry device may be implanted in the subject.

BRIEF DESCRIPTION OF THE DRAWINGS

FIG. 1 shows an overall schematic of various components of the horizontal whole body chamber (HWBC) described herein.

FIG. 2A shows the results of repeated measurement experiments with sampling performed at three locations within the chamber ranged from 7.35 to 10.65 mg/m3.

FIG. 2B shows that the average concentration over all three experiments set forth in FIG. 2A was remarkably consistent ranging from 9.19 to 9.46 mg/m3.

FIG. 2C shows dust track recordings from all three locations in the set-up from FIG. 2A over the 2-minute experiment and demonstrate consistency between all three sampling locations.

DETAILED DESCRIPTION

The present disclosure concerns an enclosed chamber suitable for whole-body (WB) exposure to an animal of any size. The horizontal whole-body chamber (HWBC) described herein provides a single animal WB exposure apparatus that includes suitability for small to medium sized animals (up to ~5 kg). While certain aspects set forth herein relate the chamber to application to smaller animals, it will be appreciated that the chamber is readily scalable to suit animals of any size. In some aspects, the HWBC as set forth herein can be utilized to observe and/or record how a test animal subject reacts or responds to whole body exposure to a test material. In other aspects, it will be apparent that the HWBC as set forth herein can be utilized for non-animal studies as well, such as in designing and/or testing sensors to detect biological and/or chemical components suspended in the atmosphere. In further aspects, the HWBC can be utilized to test the accuracy of a sensor to a test biological and/or chemical material. In some aspects the HWBC can be utilized to design or test an alarm to a particular aerosolized biological and/or chemical composition.

In some aspects, the present disclosure concerns placing a tube or duct in a horizontal orientation. In some aspects, the tube is a cylinder. However, it should be appreciated that the shape of the chamber need not be limited to a cylinder. Instead, a tube or duct as set forth for the purposes of this disclosure concerns a hollow space with smooth curved walls that extend linearly in a horizontal orientation. By placing a tube or duct, such as a cylinder, such that the length is oriented horizontally, an increased surface area is available for an enclosed test animal subject to move freely and exhibit normal behaviors and postural changes. The horizontal orientation may further allow space to place an appropriate length of duct work ensuring a uniform aerosol distribution within the chamber. It will be appreciated that the size of the interior or space for intended whole body exposure be suited to the size of the animal, as well as other considerations such as the amount of test material and desired concentration of exposure. In some aspects, the tube or duct include a proximal end, a distal end and a length or a horizontal length.

In further aspects, the tube or duct may be of a material suitable to the desired application of the chamber. In some aspects, the tube may be of a material that is inert or non-reactive to the test material. In certain aspects, the material of the tube or duct should also be resistant to any cleaning solutions, such that the chamber may retain its structural integrity for multiple uses. In other aspects, the tube or duct may be of a transparent or translucent material to allow for visualization of the test subject during a whole-body exposure time course. In further aspects, the tube or duct may be of an inert or passive material to electromagnetic radiation or radio waves. In some aspects, the test subject within the HWBC may require a connection to a device and in such aspects, the materials of the tube or duct should be of a non-interfering material, such that the connection can be wireless or shielded from interference. In certain aspects, the subject may be equipped with a telemetry device and as such, the tube or duct material should be inert to interfering with any transmitted signal. In certain aspects, the materials should not function as a shield for electromagnetic and/or radio transmissions. In some aspects, the use of radio frequency transparent materials resistant to chemical degradation throughout allows for maximum transmission of telemetry signals and decontamination with harsh chemicals. In some aspects, the tube or duct is of glass or a transparent polymer, such as polycarbonate, polyethylene terephthalate (PET), polyvinyl chloride (PVC), polymethyl methacrylate (PMMA) or acrylic or plexiglass, PET glycol (PETG), liquid silicone rubber (LSR), cyclic olefin copolymers, polyethylene (PE), transparent polypropylene (PP), ionomer resins, fluorinated ethylene propylene (FEP), styrene methyl methacrylate (SMMA), styrene acrylonitrile resin (SAN), polystyrene, methyl methacrylate acrylonitrile butadiene styrene (MABS), or combinations thereof.

In some aspects, the HWBC is configured to mix and uniformly distribute a test material within the interior space of the tube or duct. In some aspects, a test material may be an aerosolized particulate or a gas or a vapor of which the user is interested in determining results of whole body exposure thereto.

In some aspects the HWBC is equipped with at least one end cap at either end of the tube or duct. In certain aspects, the HWBC is equipped with two end caps at both ends of the tube or duct. It will be appreciated that the end cap may be either of the same or a different material from the tube or duct. The end caps can close off access to the space within the tube or duct to allow for a controlled atmosphere within the space where the test animal subject is placed. The end cap may be connected to the ends of the tube or duct with a seal, such as a gasket or an O-ring to allow for air tightness and/or to prevent leaking and/or to maintain a reduced atmospheric pressure within the chamber. In some aspects, an end cap is attached or connected to the proximal end of the tube or duct. In other aspects, an end cap is attached or connected to the distal end of the tube or duct. In further aspects, end caps are attached or connected to both the proximal and distal ends of the tube or duct.

In some aspects, the end cap may be secured to the tube or duct, either at one or both ends thereof, to provide a force between the end cap and the tube or duct to ensure minimal to no leaking from the assembled chamber. Such a retaining force can be applied through a tightened thread, such as with a bolt or screw. In some aspects a tightened thread can run along the length of the tube or duct and connect end caps to both the proximal and distal ends of the tube or duct. In other aspects, a retaining force may be applied through a clamp applied between the end cap and the proximal and/or distal end of the tube or duct.

In some aspects, the end cap may feature a taper, such that the cross-sectional diameter of the end cap increases as it approaches the tube or duct and decreases as it proceeds toward an inlet or outlet. In some aspects, the end cap may be in a conical shape or in truncated conical shape.

In some aspects, the end cap may include one or more ports or openings. Such may provide points of obtaining a sample of the test material distribution within the HWBC. Such may also allow points for inserting sensors or measuring devices, such as for obtaining a temperature value, a pressure value, a concentration value, and/or a humidity value. Further, collecting data from ports at the proximal end and the distal end may provide points of comparison to determine the uniformity or variances along the HWBC. In further aspects, the tube or duct may also include ports or sensors dispersed along the length therein to obtain further data points such as gravimetric, optical and gas/vapor values.

In further aspects, the proximal end of the tube or duct is connected to an inlet or to two or more inlets, such that a test material may be introduced into the space within the tube or duct and thereby allow for whole-body exposure to the test animal subject placed therein. The inlet may in some aspects have a valve to allow for opening and closing of the inlet. In certain aspects, the inlet is provided through an end cap placed on the proximal end of the tube or duct. In some aspects, the inlet can further be coupled to a source of forced air, such that when the inlet is open, the forced air is provided into the space within the tube. The forced air may be mixed with the test material at the inlet, prior to the inlet or after the forced air enters the HWBC in an area proximal to the inlet. In some aspects, the inlet may be positioned at or near the proximal end of the end cap, wherein the distal end of the end cap in connected to the proximal end of the tube or duct.

In some aspects, the inlet may feature or be operably connected with a nebulizer or a atomizer to achieve an initial combining of the test material within the flow of air through the HWBC. Such devices are known and understood and can be adjusted as needed to meet the parameters required by a user. For example, the rate of atomization can be increased if a user is examining the effects of increased distribution or disbursement of a test material. Similarly, particle size can be adjusted if a user is examiner the effects of particle size on the test animal subject. In other aspects the inlet may be connected or proximal to a source of a test gas or vapor such that the air from the inlet and the test material can be combined.

In some aspects, the distal end of the tube or duct is connected to an outlet, such that a test material introduced at the proximal end is allowed to exit the chamber. In certain aspects, the outlet may be operably connected to an end cap on the proximal end of the tube or duct. In further aspects, the outlet may be positioned at or near the distal end of the end cap, wherein the proximal end of the end cap is connected to the distal end of the tube or duct. In some aspects, the outlet may have a valve to allow for opening and closing of the outlet. In certain aspects, the outlet may be operably connected to a vacuum or a source of reduced air pressure, such that when the outlet is engaged or open, a negative atmospheric pressure is applied to the space within the assembled chamber. In some aspects, applying and/or maintaining a reduced atmospheric pressure within the chamber allows for a propulsion or flow or current of air throughout the chamber. In some aspects, applying a vacuum or reduced atmospheric pressure at the outlet on the proximal end of the tube or duct can draw a test material from the inlet and through the interior space of the tube or duct. In such aspects, the vacuum or reduced pressure can cause or assist with combining the test material at the inlet and effectively draw the test material through the chamber and provide a whole-body exposure to a test animal subject placed therein.

In further aspects, the HWBC may include one Stairmand disk. In other aspects, the HWBC may include two or more Stairmand disks. In certain aspects, the present disclosure concerns including at least one Stairmand disk between the inlet in a proximal end cap and the proximal end of the tube of the HWBC. The introduction of at least one Stairmand disk may provide for uniform mixing of the test material within a flow of air through the HWBC, such as that caused by a vacuum at the outlet or forced air through the inlet. In some aspects, the presence of a Stairmand disk provides for turbulence of the air as it moves from the inlet to the outlet of the HWBC. A Stairmand disk may include a plate with two or more arms that is placed or suspended before the proximal end of the tube of the HWBC. In some aspects, the plate of the Stairmand disk is the same geometric shapes as the cross-section of the tube. As air hits the plate, turbulence is created as the air vortices on the leeward side providing for improved mixing, with the air allowed to enter the tube by passing through the space between the arms of the Stairmand disk. In some aspects, the Stairmand disk has three or more arms. In further aspects, the Stairmand disk may have a diameter similar to the approximate diameter of the hollow space of the tube of the HWBC or less. In certain aspects, the diameter of a Stairmand disk may be the approximate diameter of the hollow space of the tube or duct over the square root of two or divided by approximately 1.4.

In some aspects, the presence of a Stairmand disk before the proximal end of the tube or duct of the HWBC provides sufficient turbulence to reduce the distance required from the inlet to achieve uniform distribution or disbursement of the test material in the atmosphere within the HWBC, such that the test animal subject is exposed to an evenly distributed or dispersed test material dispersed therein. In some aspects, the introduction of a Stairmand disk may reduce the distance required for achieving a homogenous distribution to about 10 times the diameter of the tube. In some aspects, the presence of a second Stairmand disk may reduce the required distance to achieve uniform disbursement and/or distribution of the test material to three times the diameter of the tube and in further aspects, the presence of a third Stairmand disk may reduce the required distance to that of about the diameter of the tube.

In some aspects, the present disclosure concerns the suspension or placement of multiple Stairmand disks between the inlet and the proximal end of the tube. In some aspects, there may be two, three, or more Stairmand disks placed between the inlet and the proximal end of the tube. In certain aspects, three Stairmand disks may be placed between the inlet and the proximal end of the tube of the HWBC.

In further aspects, the present disclosure concerns the suspension or placement of multiple Stairmand disks between the inlet and the proximal end of the tube, where each Stairmand disk is separated by a minimal distance. It will be appreciated that in order for additional Stairmand disks to meaningfully contribute to providing further turbulence to achieve a homogenous distribution of the test material, there should be sufficient space to allow any air flow from a previous Stairmand disk to create vortices on the leeward side before encountering a further Stairmand disk. In certain aspects, each Stairmand disk may be separated by a minimum distance, but it will be appreciated that an upper limit is not required or necessary. In further aspects, each Stairmand disk may be separated by a minimum distance of about 0.25-1 times the diameter of the tube or duct of the HWBC.

In certain aspects, the present disclosure concerns placement of multiple Stairmand disks between the inlet and the proximal end of the tube, wherein each Stairmand disk is placed or suspended within an end cap. In further aspects, the end cap may be tapered, such as with a truncated conical shape. In such instances, the diameter of each Stairmand disk may be of the same diameter or less as the diameter of the truncated conical shape at the point of insertion or placement therein. In further aspects, each Stairmand disk may have a diameter that is equal to the diameter at its point of placement in the end cap divided by the square root of two or approximately 1.4.

In some other aspects, the inlet may provide a source of ambient air or of forced air to allow the air to propel through the HWBC. In some aspects the inlet may include a valve to allow for shut off of forced air or of ambient air from outside the HWBC. In aspects where a vacuum may be applied at the outlet, access to ambient air or to forced air at the inlet can be required to move or propel air through the HWBC and provide uniform distribution of the test material. In some aspects, an air filter may be operably coupled to the inlet to allow for filtration of any incoming air to remove any extraneous pollutants or particles suspended therein. Suitable filters may include a HEPA filter, a washable filter, a spun glass filter, a pleated filter, an electrostatic filter, a media filter, or combinations thereof. In other aspects, the outlet may similarly possess a valve to shut off access of the interior of the HWBC to the ambient air outside. In aspects where the HWBC utilizes forced air, the outlet may need to be in communication with the ambient air outside of the HWBC to allow for air to escape or exhaust after flowing through the device. In other aspects, the outlet may be operably connected to a vacuum to draw air from the proximal end toward the distal end.

In further aspects, a propulsion or flow of air is provided to the interior of the HWBC that generally travels from the proximal to the distal ends of the HWBC. As described herein, the HWBC includes an inlet at the proximal end and an outlet at the distal end. By opening the inlet to ambient air and providing a vacuum at the outlet, or by providing forced air at the inlet and opening the outlet to ambient air or by applying both forced air at the inlet and a vacuum at the outlet, a user is able to generate a propulsion of air that flows generally from the proximal end to the distal end of the HWBC. As the propulsion of air within the HWBC originates at the inlet, placing an atomizer or nebulizer or similar to aerosolize a test material near the inlet allows for the propulsion of air to catch aerosolized test material and move the test material through the HWBC as the flow of air propels toward the outlet. Similarly, placing a valve for a test gas or vapor near the inlet allows for the test material to combine with the flow of air. As further set forth herein, the presence of one or more Stairmand disks provides vortices on their leeward side that compel mixing of the test material within the flow of the propelled air as it ultimately moves toward the outlet.

In further aspects, the tube or duct may include a platform therein. As the tube or duct includes curved walls, it may be of interest to the user to provide a horizontal platform for the test animal subject to allow for improved balance or comfort for the test animal subject when placed within the HWBC. As with the tube or duct material, the platform can be of any material. In some aspects, the platform can be inert or non-reactive to the test material and/or a cleaning material. It will also be appreciated that the presence of a horizontal platform provides a surface upon which a feeding or drinking bowl or receptacle may be placed. In some aspects, the horizontal platform may be of a perforated or mesh or grated material to allow for any excretions by the test animal subject to fall into and away from the feet of the test subject animal.

In some aspects, the HWBC may include a screen or grate placed between the inlet and the proximal end of the tube or duct. In other aspects, the HWBC may include a screen or grate placed between the outlet and the distal end of the tube or duct. In certain aspects, the HWBC may include a screen or grate placed between the inlet and the proximal end of the tube or duct and a second screen placed between the distal end of the tube or duct and the outlet. It will be appreciated that including a screen or grate can provide a physical barrier to retain the test animal subject within the tube or duct. Retaining the test animal subject within the tube or duct can function to ensure the whole body exposure occurs at a point where the test material is uniformly distributed with the air flow, as well as serve the general safety and well-being of the test animal subject. In some aspects, a Stairmand disk can be connected or mounted to a screen or grate. It will be appreciated that the screen or grate be a sufficient barrier to prevent the intended test animal subject from passing through, but should not be significantly small so as to prevent or minimize any potential interference with the propulsion or flow of air and the test material homogenously dispersed therein. In other aspects, the screen or grate is of a material that is inert or non-reactive to the test material. In further aspects, the screen or grate is resistant to potential build-up of static charge to avoid or minimizing any unwanted static attraction to the test material. In other aspects, the HWBC as described herein can be utilized for non-animal purposes such as for the design, calibration and/or testing of a sensor or alarm to a test material. In such aspects it will be appreciated that the screen need not be utilized.

In some aspects, the present disclosure also concerns methods for performing whole-body exposure of a test material on a test animal subject. In some aspects, the methods may include assembling the HWBC as described herein. Such assembly may including placing an end cap on the proximal end of the tube or duct and/or on the distal end of the tube or duct. Such may also include securing the end caps to the tube or duct. Such may also include the placement of a gasket or O-ring between the end cap and the end of the tube or duct. Such may also include operably connecting a source of forced air, such as a compressor, to the inlet and/or a vacuum to the outlet. Such may also include opening a valve at the inlet and/or outlet. Such may also include placing a platform within the tube or duct. Such may also including inserting sensors or measurement devices in ports on the proximal end cap and/or distal end cap. Such may include devices such as thermometers, barometers, and aerosol monitors within the ports or along the length of the tube or duct.

In other aspects, the methods may include placing one or more test animal subjects within the tube or duct area of the HWBC and then providing a propulsion or current of air through the interior of the HWBC. As described herein, the propulsion or current of air may be created by a vacuum applied at the outlet and/or by applying forced air at the inlet. The propulsion or current of air may be sustained by maintaining the forced air and/or vacuum at the appropriate points of entry into the HWBC. An atomizer or nebulizer can be activated to aerosolize a test particulate material and by placement in proximity to the inlet, the test material can become suspended within the propulsion of air. A test gas or vapor can be similarly combined with the air flow by placing a valve or nozzle near the inlet. As also described herein, as the propulsion or current of air migrates toward the outlet, the placement of Stairmand disks between the inlet and the proximal end of the tube or duct allows for uniform disbursement or distribution of the test material within the propulsion of air. In some aspects, placing three Stairmand disks between the inlet and the proximal end of the tube or duct allows for uniform distribution or disbursement of the test material by the point at which the propulsion or current of air reaches the interior of the tube or duct, which is the zone in which the test animal subject resides. By providing uniform distribution or disbursement of the test material by the point at which the propulsion of air reaches the interior of the tube or duct, the position of the animal within the tube or duct is not required for identifying the level of whole body exposure.

In some aspects, the methods may include one or more operating parameters. Most operating parameters may be determined by the user, for example the choice of test material, the particle size of the test material, the concentration of test material, the type of animal chosen, the temperature of the interior of the HWBC can be parameters that are varied or controlled for during the whole body exposure. Certain parameters though may need to be further controlled to ensure accurate exposure and safety, such as the rate of air flow and the air pressure within the HWBC.

In some aspects, the methods include operating the propulsion or current of air flowing through the tube or duct at a rate of about 1 to about 3 linear feet per minute (LFM), including about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, and 2.9 LFM. In certain aspects the flow of air within the HWBC may be of from about 1.29 LFM to about 2.60 LFM. It will be understood that the flow or current of air within the HWBC should be a sufficiently high rate so as to ensure that test materials uniformly distributed therein and can remain suspended therein without precipitating or separating from the air flow or propulsion. It should be further appreciated that the rate of air flow should remain low so as to avoid discomfort to the test animal subject and risk reducing the accuracy of the whole body exposure. For example, a high rate of air flow may cause the animal to face the distal end of the tube or duct and effectively shelter the respiratory system from exposure.

In further aspects, the methods may include operating the flow or current of air within the HWBC at a negative barometric air pressure within the HWBC. As described herein, the HWBC may include end caps connected to the tube or duct. In some aspects, it may be of benefit to introduce a negative air pressure within the HWBC to prevent any air leaking and/or to prevent any ambient air from entering the HWBC from unintended points. In some aspects, the pressure within the HWBC can kept at a negative air pressure by affixing a vacuum to the outlet or a port of the HWBC. In other aspects, a negative pressure can be maintained by including an air pump within the HWBC that is connected to a port or outlet to exhaust air from the interior of the HWBC. In some aspects, the methods may include operating the flow of air in the HWBC at a negative pressure of up to about −0.8 inches of water, including about −0.05, −0.1, −0.15, −0.2, −0.25, −0.3, −0.35, −0.4, −0.45, −0.5, −0.55, −0.6, −0.65, −0.7, and −0.75 inches of water. In certain aspects the pressure may be maintained at from about −0.5 to about −0.8 inches of water.

In further aspects, the methods may include operating the flow or current of air within the HWBC at a neutral or positive barometric air pressure within the HWBC. As described herein, the end cap can be forcefully secured to the distal and/or proximal end of the tube or duct, thereby allowing for increased barometric pressure within the HWBC. It will be appreciated that the upper pressure limits can be determined by the force and tightness of the seal between the end cap and the tube or duct, as well as by any limitations present in the materials used.

In some aspects, the methods of the present disclosure concern use of the HWBC for non-animal purposes, such as designing, calibrating or testing a sensor or alarm to the test material. By operating the HWBC as described herein, it is possible to place a sensor or alarm to the test material within the tube or duct and examine the response by the sensor or alarm to the presence of the test material and/or to a certain concentration of the test material dispersed homogenously within the atmosphere contained by the HWBC.

Turning now to FIG. 1, depicted is an exemplary HWBC 100 as described herein. Particularly, a tube or duct 20 is flanked by a proximal end cap 2 and a distal end cap 11. On the proximal end cap 2 an inlet 1 is provided to allow for air to propel through the HWBC 100. A valve (not shown) at the inlet 1 can allow for forced air or ambient air to enter the HWBC 100. A threaded rod 9 can retain the proximal end cap 2 and the distal end cap 11 against the ends to the tube or duct 20. A seal 14 may be placed between the proximal end cap 2 and the tube or duct 20 to limit any air leaks or disturbance from ambient air outside the HWBC 100 to air flowing through the interior of the HWBC 100. A second seal 15 may also be placed between the distal end cap 11 and the tube or duct 20 to serve a similar purpose.

As also depicted in FIG. 1, at least one Stairmand disk 4 is placed or suspended between the inlet 1 and the relevant end of the tube or duct 20 to provide mixing of air flowing in from the inlet 1 with an aerosolized test material (not depicted). A screen 3 may further be put in place of the air flow as it travels from the inlet 1 into the tube or duct 20.

The HWBC 100 further includes an outlet 13 that withdraws air from the interior of the HWBC 100 either through an applied vacuum or into the ambient air outside the HWBC 100. The outlet 13 may feature on an end of the distal end cap 11. In addition to the outlet 13, the distal end cap 11 may include one or more ports 12 that allow for access to the flow of air within the HWBC 100 and a second screen 10. Additional points of access (not depicted) may also be included within the proximal end cap 2 in a similar manner. Further sampling points or sensors 5, 7, 8 may feature along the length of the tube or duct 20 to provide additional access and/or data concerning the air flow through the HWBC 100.

EXAMPLES

The initial HWBC was designed to be operated at a pressure of −0.50" to −0.75" of water and at ~30 L/min of airflow based on the final volume of the chamber. The configuration presented is set up to be able to generate particle aerosols, gas/vapor atmospheres or a combination of the two. Chemical aerosols were generated with a double needle atomization device operated at an airflow of 1.0 L/min. Vapor/gas atmospheres were generated from tanked sources or vaporized off liquids. Mixed atmospheres were combined at the point of aerosol generation to ensure even mixing. At the point of gas/vapor generation, a ¾" swage lock tee fitting was placed inline allowing for a supply of HEPA filtered makeup air to mix with atomized material which then entered a stainless steel (SS) cone stepping up the diameter from 2" to 4". The cone was connected to a short mixing chamber consisting of two Stairmand disks contained at each end of a 6" section of 4" diameter SS pipe. This expansion chamber then connected to the inlet cone of the HWBC.

The HWBC featured three main components, the inlet cone, animal zone, and outlet cone. The inlet and outlet cones were constructed of DSM Somos 9120 Photo polymer, and provided a connection between in the 4" SS inlet tubing and a 9.25" glass animal zone. The cone included a channel filled with a urethane rubber gasket (PMC-121-30, Reynolds Advanced Materials, Allentown, PA) which formed a seal with the glass. A grate with a further Stairmand disk attached (constructed of DSM Somos 9120 Photo polymer) served to keep animals from entering the inlet cone and created a final point of turbulence for mixing of the atmosphere upon entry to the animal zone. The animal zone was constructed of tempered glass and measured 9.25" dia.×14"L×¼" thick. It contained a plastic grate placed in the bottom to support the animal and was itself supported on PLA plastic legs which also house the bottom portion of the latching mechanism. The outlet cone was a mirror image of the inlet cone in design and shape but it also contained 8 sampling ports. It also contained a grate to keep the animal from entering the outlet cone which was connected to a 4" SS plate with a ¾" swage lock fitting connected to ¾" plastic tubing which served to supply vacuum which operated the chamber. The sampling ports allowed for connection of gravimetric, optical and gas/vapor sampling devices for characterization of the atmosphere.

The outlet cascade of the HWBC began with ¾" plastic tubing that was connected to the outlet cone of the chamber. From there the tubing connected to an inline HEPA filter backed up with an inline carbon filter. This was followed by passage through a Hastings LI-1D laminar flow element, connection to two 30 L/min mass flow controllers (Model 5158E Brooks Instrument, Hatfield, PA) and finally connected to a vacuum pump (Model 2567B, Welch Inc., Sheboygan, WI). The exhaust from the vacuum pump was then plumbed through a second carbon filter and back into the chemical fume hood.

Two methods of distribution analysis were employed to characterize the aerosol distribution within the HWBC. The first method was a series of repeated measurements to determine aerosol concentrations in the middle of the chamber. For this protocol, an aerosol of dexmedetomidine HCl was generated and allowed to stabilize, as indicated by a DustTrak II Aerosol Monitor (Model 8530, TSI Inc., Shoreview, MN). Once the aerosol concentration stabilized, one glass fiber filter sample was collected simultaneously from each of three ¼" SS sampling tubes located at points 5, 7, and 8 in FIG. 1, in the center of the chamber and 2.5 cm, 17.5 cm and 33 cm from the inlet screen respectively. This test was repeated on three different days using the same aerosolization solution and generator settings for a total of three samples per sampling location. Following collection of aerosol samples, the precise concentration of material at each sampling site was determined by analytical chemistry.

The second method of distribution analysis was designed to detect the effect of the chamber edge on the aerosol concentration, which is designated here by the term edge-effect sampling. For this protocol, a stable aerosol was generated, as indicated by the DustTrakII aerosol monitor. Once the aerosol concentration stabilized, each of the three different length tubes, from the repeated measures test, were changed in orientation and the DustTrakII reading was monitored for two minutes. For example, the inlet sampling tube was rotated to nearly touch (~¼" stand-off) the side of the animal chamber on the left, then rotated to nearly touch the side of the animal chamber on the right, then elevated to nearly touch the top of the animal chamber and lowered to nearly touch the floor of the chamber. The same procedure was performed for the other two sampling tubes and the results were manually tabulated.

Glass fiber filters were extracted by adding 1 mL of methanol to the sample and allowing it to extract for a minimum of 15 minutes. The extracts from both the glass fiber filters and the stainless steel plates were diluted as necessary with methanol in 2 mL glass autosampler vials (Agilent Technologies, Santa Clara, CA), spiked with isotopically labelled internal standards, mixed using a vortex mixer on a high setting for 30 seconds, and transferred to autosampler trays for analysis using LC/MS/MS technologies.

Samples were analyzed using an Agilent 1290 Infinity Series Binary Pump Ultra-High Performance Liquid Chromatograph (UHPLC) Model G4220A interfaced with an Agilent 6490 Triple Quadrupole Mass Spectrometer (Agilent Technologies, Santa Clara, CA). Injections of 1 μL of extract were made using an acetonitrile solvent wash in the FlushPort for 10 seconds to prevent carryover. Injections were made with a constant flow rate of 0.2 mL/min through a BEH $C_8$ Column (Waters, Inc.) 2.1 mm×50 mm, 1.7 μm df with the column compartment held at room temperature. The solvents were 0.1% Formic Acid/$H_2O$ (A) and 0.1% Formic Acid/Methanol (B). The LC gradient program was initially 2% B (2 min. hold) going to 90% B (2 min. gradient) and holding for 0.5 minute, then back to 2% B (1 minute gradient, 0.5 minute hold) to re-equilibrate the column for a run time of 6 minutes total.

Detection was performed using positive ion electrospray ionization with Agilent Jet Stream followed by Multiple Reaction Monitoring (MRM) analysis and data was collected for MRM ion transitions for each compound and for the deuterated internal standard. The method utilized a drying gas temperature of 225° C., drying gas flow of 15 L/min, nebulizer pressure of 20 psi, sheath gas heater set to 250° C., sheath gas flow of 9 L/min, capillary voltage of 1500V, Vcharging set to 500V, and electron multiplier delta of +100V. Ion transitions were collected using unit resolution with a fragmentor voltage of 380V, collision energy of 22V for each transition, cell accelerator voltage of IV, and a dwell time of 50 ms/cycle. The ion transitions collected were dexmedetomidine 201.2>132.9, and D4-Decmedetomidine 205.2>137.0.

Figure 2A:
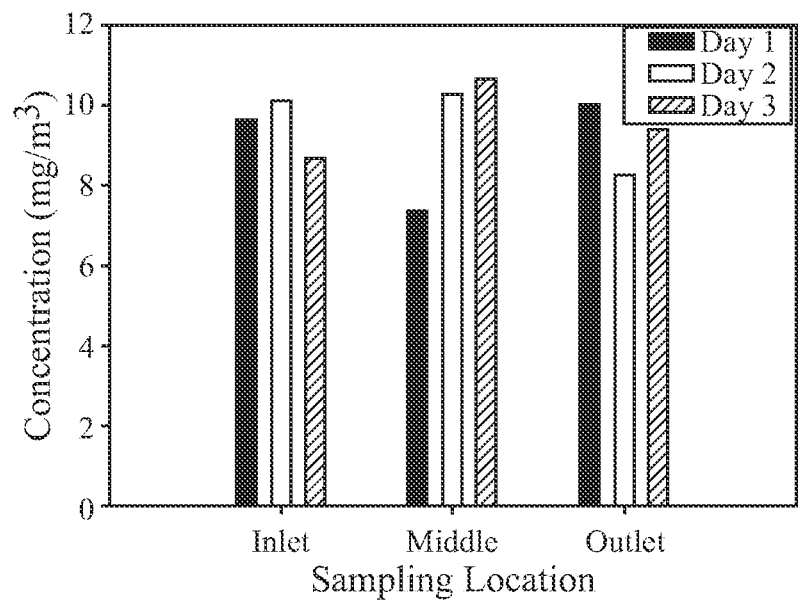
Figure 2B:
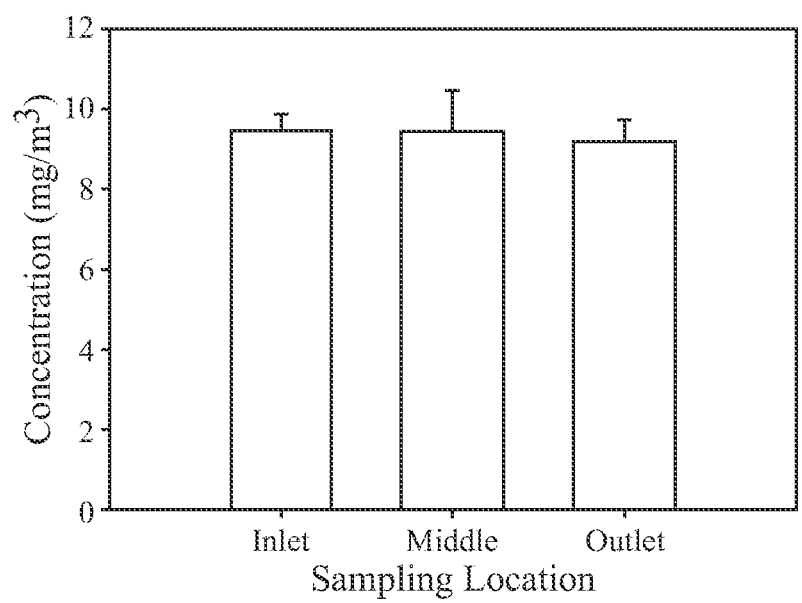
Figure 2C:
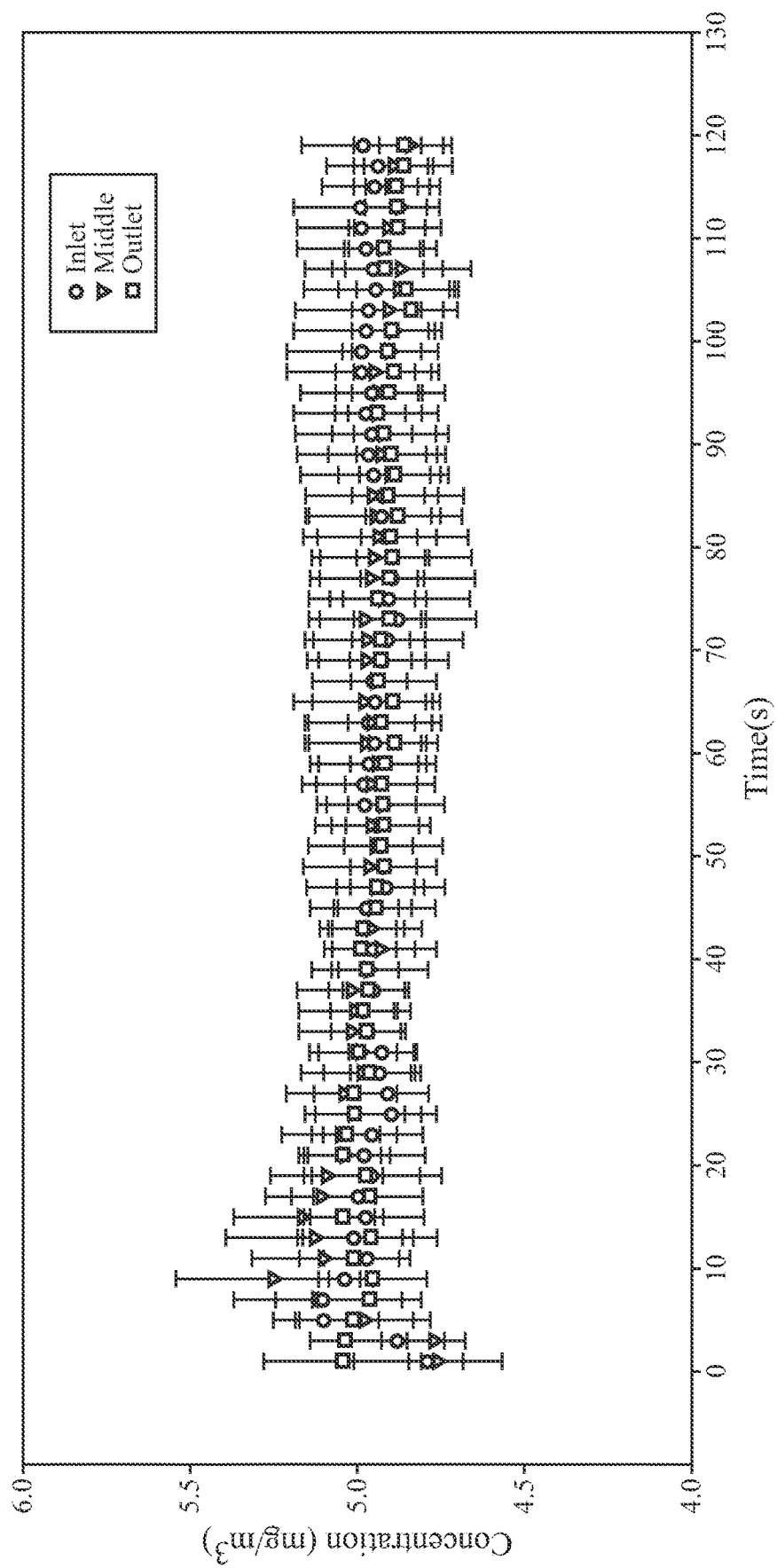

The performance and distribution characteristics of the HWBC were evaluated by generating a solid particle aerosol from a solution of dexmedetomidine hydrochloride and ethyl alcohol. Repeated measurement experiments with sampling performed at three locations within the chamber ranged from 7.35 to 10.65 mg/m3 (FIG. 2a). The average concentration over all three experiments was remarkably consistent ranging from 9.19 to 9.46 mg/m3 (FIG. 2B). Finally, dust track recordings from all three locations over the 2-minute experiment indicate consistency between all three sampling locations (FIG. 2C).

Sampling from locations near the edges of the chamber and comparing this to measurements from the center of the chamber was deemed a reasonable method to determine heterogeneity in the aerosol due to edge effects of airflow through the chamber. The data from the edge effects experiment indicates homogeneity of the aerosol, with a range of 0.69-0.75 mg/m3 across all locations sampled via DustTrakII recordings during the experiment (Table 1). The maximum percent difference between all locations is 8.3%.

TABLE 1

Average DustTrakII measurements from a 2-minute sample at each orientation

| | Top (SEM) | Bottom (SEM) | Left (SEM) | Right (SEM) | Center (SEM) |
| --- | --- | --- | --- | --- | --- |
| Inlet Tube (mg/m³) | 0.73 (0.006) | 0.73 (0.012) | 0.69 (0.004) | 0.71 (0.010) | 0.72 (0.011) |
| Middle Tube (mg/m³) | 0.72 (0.008) | 0.69 (0.008) | 0.71 (0.009) | 0.69 (0.020) | 0.72 (0.021) |
| Outlet Tube (mg/m³) | 0.71 (0.029) | 0.75 (0.023) | 0.74 (0.013) | 0.75 (0.017) | 0.73 (0.021) |

The foregoing description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Patents, applications, and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular aspects of the invention, but is not meant to be a limitation upon the practice thereof. The following claims, including all equivalents thereof, are intended to define the scope of the invention.

We claim:

1. An enclosed chamber, comprising:

a horizontal chamber tube operably connected at a proximal end to a first end cap and at a distal end to a second end cap, wherein the horizontal chamber tube comprises a material with a cross sectional dimension that defines a hollow space along the length of the horizontal chamber tube, the first end cap comprising an inlet and at least one Stairmand disk, and the second end cap comprising an outlet, and further wherein the inlet and the outlet are operably connected through the hollow space to allow passage of a test gas through the enclosed chamber and further wherein the enclosed chamber is configured to disperse an aerosol uniformly within 1 to 3 cm of the proximal end of the horizontal chamber tube.

2. The enclosed chamber of claim 1, wherein the first end cap comprises at least two Stairmand disks.

3. The enclosed chamber of claim 1, wherein the first end cap comprises at least three Stairmand disks.

4. The enclosed chamber of claim 1, wherein the first end cap further comprises a screen.

5. The enclosed chamber of claim 1, wherein the first end cap is connected to the horizontal chamber tube through a mechanical seal.

6. The enclosed chamber of claim 5, wherein the mechanical seal is an O-ring or a gasket.

7. The enclosed chamber of claim 1, wherein a vacuum source is attached to the outlet.

8. The enclosed chamber of claim 1, wherein a forced air source is attached to the inlet.

9. The enclosed chamber of claim 1, wherein the first end cap and the second end cap are retained against the horizontal chamber tube by an applied force.

10. The enclosed chamber of claim 9, wherein a threaded rod or a clamp is placed on the first end cap and/or second end cap for the applied force.

11. The enclosed chamber of claim 1, wherein the inlet and outlet are configured to provide a test gas flow of between 1 to 3 linear feet per minute through the enclosed chamber.

12. The enclosed chamber of claim 1, further comprising at least one sensor placed in the hollow space.

13. The enclosed chamber of claim 1, wherein the hollow space is in a horizontal cylinder shape.

14. The enclosed chamber of claim 1, wherein the horizontal chamber tube comprises glass, steel, or an organic polymer.

15. The enclosed chamber of claim 1, wherein the first end cap and the second end cap are of a truncated conical shape.

16. The enclosed chamber of claim 1, wherein one or more ports are present on the first end cap and/or the second end cap to access the test gas.

17. The enclosed chamber of claim 1, wherein the test gas comprises a particle aerosol or a gas atmosphere.

18. A method for assessing whole-body exposure to a test gas in a subject, comprising:

placing the subject in the hollow space of the enclosed chamber of claim 1;

providing the test gas at the inlet;

providing a source to cause the test gas to flow through the hollow space of the enclosed chamber; and exposing the subject for a test period of time under controlled temperature parameters.

19. The method of claim 18, wherein the source comprises a forced air source at the inlet or a vacuum source at the outlet.

20. The method of claim 19, wherein the vacuum is at a pressure to move the test gas through the enclosed chamber at a rate of 1 to 3 linear feet per minute.

21. The method of claim 18, further comprising obtaining a sample of the test gas from the enclosed chamber during the test period of time.

22. The method of claim 18, further comprising implanting a telemetry device in the subject.

* * * * *